(12) United States Patent
Remstein et al.

(10) Patent No.: US 7,618,781 B2
(45) Date of Patent: Nov. 17, 2009

(54) NUCLEIC ACIDS FOR DETECTING B-CELL MALIGNANCY

(75) Inventors: Ellen D. Remstein, Rochester, MN (US); Richard R. Einerson, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 170 days.

(21) Appl. No.: 11/747,290

(22) Filed: May 11, 2007

(65) Prior Publication Data

US 2007/0264657 A1 Nov. 15, 2007

Related U.S. Application Data

(60) Provisional application No. 60/799,810, filed on May 12, 2006.

(51) Int. Cl.
  *C12Q 1/68* (2006.01)
  *C12N 15/13* (2006.01)
(52) U.S. Cl. .................................. 435/6; 536/24.31
(58) Field of Classification Search ................. None
  See application file for complete search history.

(56) References Cited

U.S. PATENT DOCUMENTS

2003/0129626 A1* 7/2003 Nielsen et al. ............... 435/6

OTHER PUBLICATIONS

Kennell, Progr. Nucl. Acid Res. Mol. Biol. 11: 259 (1971).*
GenBank Accession No. AC000029, dated Apr. 9, 2003, 42 pgs.
GenBank Accession No. AC002060, dated Apr. 9, 2003, 48 pgs.
GenBank Accession No. AC002308, dated Apr. 6, 2003, 44 pgs.
GenBank Accession No. AC007860, dated Jan. 31, 2002, 69 pgs.
GenBank Accession No. AC009958, dated Apr. 21, 2005, 61 pgs.
GenBank Accession No. AC011257, dated Dec. 4, 2001, 66 pgs.
GenBank Accession No. AC012671, dated Apr. 30, 2005, 58 pgs.
GenBank Accession No. AC022849, dated Dec. 11, 2001, 54 pgs.
GenBank Accession No. AC022973, dated Sep. 6, 2001, 69 pgs.
GenBank Accession No. AC062029, dated Apr. 21, 2005, 39 pgs.
GenBank Accession No. AC067844, dated Nov. 5, 2001, 56 pgs.
GenBank Accession No. AC073416, dated Apr. 16, 2005, 40 pgs.
GenBank Accession No. AC092836, dated Apr. 15, 2005, 49 pgs.
GenBank Accession No. AC096579, dated Apr. 30, 2005, 52 pgs.
GenBank Accession No. AC096767, dated Apr. 30, 2005, 42 pgs.
GenBank Accession No. AC100822, dated Mar. 12, 2002, 66 pgs.
GenBank Accession No. AC104081, dated Apr. 30, 2005, 42 pgs.
GenBank Accession No. AC104134, dated Apr. 30, 2005, 34 pgs.
GenBank Accession No. AC110080, dated Apr. 21, 2005, 51 pgs.
GenBank Accession No. AC116654, dated Apr. 30, 2005, 35 pgs.
GenBank Accession No. AQ015089, last updated Jun. 9, 1998, 2 pgs.
GenBank Accession No. AQ015092, last updated Jun. 9, 1998, 2 pgs.
GenBank Accession No. AQ021832, last updated Jun. 9, 1998, 2 pgs.
GenBank Accession No. AQ021835, last updated Jun. 9, 1998, 2 pgs.
GenBank Accession No. AQ069562, last updated Aug. 4, 1998, 2 pgs.
GenBank Accession No. AQ072886, last updated Aug. 5, 1998, 2 pgs.
GenBank Accession No. AQ081735, last updated Apr. 20, 1999, 2 pgs.
GenBank Accession No. AQ081737, last updated Apr. 20, 1999, 2 pgs.
GenBank Accession No. AQ099890, last updated Aug. 27, 1998, 2 pgs.
GenBank Accession No. AQ100222, last updated Aug. 27, 1998, 2 pgs.
GenBank Accession No. AQ152119, last updated Oct. 8, 1998, 2 pgs.
GenBank Accession No. AQ182758, last updated Oct. 28, 1998, 2 pgs.
GenBank Accession No. AQ194866, last updated Apr. 20, 1999, 2 pgs.
GenBank Accession No. AQ194870, last updated Apr. 20, 1999, 2 pgs.
GenBank Accession No. AQ194873, last updated Apr. 20, 1999, 2 pgs.
GenBank Accession No. AQ261818, last updated Oct. 24, 1998, 2 pgs.
GenBank Accession No. AQ261819, last updated Oct. 24, 1998, 2 pgs.
GenBank Accession No. AQ263966, last updated Oct. 27, 1998, 2 pgs.
GenBank Accession No. AQ263972, last updated Oct. 27, 1998, 2 pgs.
GenBank Accession No. AQ310297, last updated Dec. 22, 1998, 2 pgs.
GenBank Accession No. AQ310298, last updated Dec. 22, 1998, 2 pgs.
GenBank Accession No. AQ316551, last updated Dec. 22, 1998, 2 pgs.
GenBank Accession No. AQ342516, last updated May 6, 1999, 2 pgs.
GenBank Accession No. AQ342518, last updated May 6, 1999, 2 pgs.
GenBank Accession No. AQ347596, last updated May 7, 1999, 2 pgs.
GenBank Accession No. AQ347598, last updated May 7, 1999, 2 pgs.
GenBank Accession No. AQ348887, last updated May 7, 1999, 2 pgs.
GenBank Accession No. AQ348888, last updated May 7, 1999, 2 pgs.
GenBank Accession No. AQ353302, last updated Jan. 24, 1999, 2 pgs.
GenBank Accession No. AQ404544, last updated Mar. 13, 1999, 2 pgs.
GenBank Accession No. AQ411280, last updated Mar. 17, 1999, 2 pgs.
GenBank Accession No. AQ482936, last updated Apr. 24, 1999, 2 pgs.
GenBank Accession No. AQ482939, last updated Apr. 24, 1999, 2 pgs.
GenBank Accession No. AQ488474, last updated Apr. 24, 1999, 2 pgs.
GenBank Accession No. AQ488477, last updated Apr. 24, 1999, 2 pgs.
GenBank Accession No. AQ529915, last updated May 18, 1999, 2 pgs.
GenBank Accession No. AQ529916, last updated May 18, 1999, 2 pgs.

(Continued)

*Primary Examiner*—James Martinell
(74) *Attorney, Agent, or Firm*—Fish & Richardson P.C.

(57) ABSTRACT

This document provides methods and materials related to detecting gene rearrangements (e.g., MYC gene rearrangements). For example, nucleic acid probe sets for detecting MYC-immunoglobulin gene rearrangements in mammals are provided.

17 Claims, No Drawings

OTHER PUBLICATIONS

GenBank Accession No. AQ561069, last updated May 29, 1999, 2 pgs.
GenBank Accession No. AQ564481, last updated May 29, 1999, 2 pgs.
GenBank Accession No. AQ632870, last updated Jun. 17, 1999, 2 pgs.
GenBank Accession No. AQ632900, last updated Jun. 17, 1999, 2 pgs.
GenBank Accession No. AQ673675, last updated Jun. 24, 1999, 2 pgs.
GenBank Accession No. AQ680759, last updated Jun. 25, 1999, 2 pgs.
GenBank Accession No. AQ800116, last updated Aug. 9, 1999, 2 pgs.
GenBank Accession No. AQ812128, last updated Aug. 25, 1999, 2 pgs.
GenBank Accession No. AQ813522, last updated Aug. 25, 1999, 2 pgs.
GenBank Accession No. AQ827727, last updated Aug. 27, 1999, 2 pgs.
GenBank Accession No. AQ894131, last updated Nov. 10, 1999, 2 pgs.
GenBank Accession No. AQ894132, last updated Nov. 10, 1999, 2 pgs.
GenBank Accession No. AZ303171, last updated Dec. 1, 2000, 2 pgs.
GenBank Accession No. AZ303172, last updated Dec. 1, 2000, 2 pgs.
GenBank Accession No. BH817039, last updated May 8, 2002, 2 pgs.
Achuthan et al., "Novel Translocation of the *BCL10* Gene in a Case of Mucosa Associated Lymphoid Tissue Lymphoma," *Genes, Chromosomes & Cancer*, 2000, 29:347-349.
Adachi et al., "Preferential linkage of BCL-2 immunoglobulin light chain gene in chronic lymphocytic leukemia," *J. Exp. Med.*, 1990, 171:559-564.
Adachi et al., "Variant translocation of the *bcl-2* gene to immunoglobulin λ light chain gene in chronic lymphocytic leukemia," *Proc. Natl. Acad. Sci. USA*, 1989, 86:2771-2774.
Akasaka et al., "Application of Long-Distance Polymerase Chain Reaction to Detection of Junctional Sequences Created by Chromosomal Translocation in Mature B-Cell Neoplasms," *Blood*, 1996, 88(3):985-994.
Akasaka et al., "Molecular Anatomy of *BCL6* Translocations Revealed by Long-Distance Polymerase Chain Reaction-based Assays," *Cancer Res.*, 2000, 60:2335-2341.
Akasaka et al., "Polymerase chain reaction amplification of long DNA targets: Application to analysis of chromosomal translocations in human B-cell tumors (Review)," *Int. J. Oncol.*, 1998, 12:113-121.
Harnden et al. (eds.), "Report of the Standing Committee on Human Cytogenetic Nomenclature," *An International System for Human Cytogenetic Nomenclature*, 1985, 120 pages.
Au et al., "Cytogenetic Analysis in Mantle Cell Lymphoma: A Review of 214 Cases," *Leuk. Lymph.*, 2002, 43(4):783-791.
Au et al., "The Spectrum of Lymphoma with 8q24 Aberrations: A Clinical, Pathological and Cytogenetic Study of 87 Consecutive Sases," *Leuk. Lymph.*, 2004, 45(3):519-528.
Avet-Loiseau et al., "Cytogenetic, interphase, and multicolor fluorescence in situ hybridization analyses in primary plasma cell leukemia: a study of 40 patients at diagnosis, on behalf of the Intergroupe Francophone du Myélome and the Groupe Français de Cytogénétique Hématologique," *Blood*, 2001, 97:822-825.
Avet-Loiseau et al., "Rearrangements of the *c-myc* oncogene are present in 15% of primary human multiple myeloma tumors," *Blood*, 2001, 98:3082-3086.
Barth et al., "Homogeneous immunophenotype and paucity of secondary genomic aberrations are distinctive features of endemic but not of sporadic Burkitt's lymphoma and diffuse large B-cell lymphoma with *MYC* rearrangement," *J. Pathol.*, 2004, 203:940-945.
Bergsagel and Kuehl, "Chromosome translocations in multiple myeloma," *Oncogene*, 2001, 20:5611-5622.
Bernard et al., "Molecular mechanisms of a t(8;14)(q24;q11) translocation juxtaposing c-myhc and TcR-alpha genes in T-cell leukemia: involvement of a V alpha internal heptamer," *Oncogene*, 1988, 2:195-200.

Bernheim et al., "Cytogenetic Studies on African Burkitt's Lymphoma Cell Lines: t(8;14), t(2;8) and t(8;22) Translocations," *Cancer Genet. Cytogenet.*, 1981, 3:307-315.
Bernheim et al., "Cytogenetic Studies on Burkitt's Lymphoma Cell Lines," *Cancer Genet. Cytogenet.*, 1983, 8:223-229.
Bornkamm et al., "*c-myc* Deregulation by Chromosomal Translocation in Burkitt's Lymphoma," *Cellular Oncogene Activation*, 1988, Chapter 7, pp. 223-273.
Bornkamm et al., "Epstein-Barr Virus-positive Burkitt's Lymphoma in a German Woman During Pregnancy," *Blut*, 1980, 40:167-177.
Brensing-Küppers et al., "The human immunoglobulin κ locus on yeast artificial chromosomes (YACs)," *Gene*, 1997, 191:173-181.
Cario et al., "Variant translocations in sporadic Burkitt's lymphoma detected in fresh tumour material: analysis of three cases," *Br. J. Haematol.*, 2000, 110:537-546.
Cataldo et al., "Detection of t(2;5) in Anaplastic Large Cell Lymphoma. Comparison of Immunohistochemical Studies, FISH, and RT-PCR in Paraffin-Embedded Tissue," *Am. J. Surg. Pathol.*, 1999, 23(11):1386-1392.
Chesi et al., "Frequent Dysregulation of the *c-maf* Proto-Oncogene at 16q23 by Translocation to an Ig Locus in Multiple Myeloma," *Blood*, 1998, 91(12):4457-4463.
Corcoran et al., "Dysregulation of cyclin dependent kinase 6 expression in splenic marginal zone lymphoma through chromosome 7q translocations," *Oncogene*, 1999, 18:6271-6277.
Cory, "Activation of cellular oncogenes in hematopoietic cells by chromosome translocation," *Adv. Cancer Res.*, 1986, 47:189-234.
Dewald et al., "The Efficacy of Direct, 24-Hour Culture, and Mitotic Synchronization Methods for Cytogenetic Analysis of Bone Marrow in Neoplastic Hematologic Disorders," *Cancer Genet. Cytogenet.*, 1985, 18:1-10
Drach et al., "The biology of multiple myeloma," *J. Cancer Res. Clin. Oncol.*, 2000, 126:441-447.
Dunphy et al., "Mature B-Cell Acute Lymphoblastic Leukemia With Associated Translocations (14;18)(q32;q21) and (8;9)(q24;p13). A Burkitt Variant?" *Arch. Pathol. Lab. Med.*, 2003, 127:610-613.
Einerson et al., "FISH Is Superior to PCR in Detecting t(14;18)(q32;q21)-*IgH/bcl-2* in Follicular Lymphoma Using Paraffin-Embedded Tissue Samples," *Am. J. Clin. Pathol.*, 2005, 124:421-429.
Fabris et al., "Heterogeneous Pattern of Chromosomal Breakpoints Involving the *MYC* Locus in Multiple Myeloma," *Genes, Chromosomes & Cancer*, 2003, 37:261-269.
Finger et al., "Chromosomal translocation in T-cell leukemia line HUT 78 results in a *MYC* fusion transcript," *Proc. Natl. Acad. Sci. USA*, 1988, 85:9158-9162.
Finver et al., "Sequence analysis of *MYC* oncogene involved in the t(8;14)(q24;q11) chromosome translocation in a human leukemia T-cell line indicates that putative regulatory regions are not altered," *Proc. Natl. Acad. Sci. USA*, 1988, 85:3052-3056.
Haralambieva et al., "Detection by the fluorescence in situ hybridization technique of *MYC* translocations in paraffin-embedded lymphoma biopsy samples," *Br. J. Haematol.*, 2003, 121:49-56.
Haralambieva et al., "Interphase Fluorescence In Situ Hybridization for Detection of 8q24/MYC Breakpoints on Routine Histologic Sections: Validation in Burkitt Lymphomas from Three Geographic Regions," *Genes, Chromosomes & Cancer*, 2004, 40:10-18.
Hayette et al., "In B-cell chronic lymphocytic leukemias, 7q21 translocations lead to overexpression of the *CDK6* gene," *Blood*, 2003, 102(4):1549-1550.
Henglein et al., "Burkitt's Lymphoma Variant Translocations: Distribution of Chromosomal Breakpoints and Perturbated Regulation of a Mutated *c-myc* Gene," *Curr. Topics Microbiol. Immunol.*, 1998, 141:165-171.
Henglein et al., "Three Breakpoints of Variant t(2;8) Translocations in Burkitt's Lymphoma Cells Fall within a Region 140 Kilobases Distal from *c-myc*," *Mol. Cell. Biol.*, 1989; 9(5):2105-2113.
Joos et al., "Variable breakpoints in Burkitt lymphoma cells with chromosomal t(8;14) translocation separate *c-myc* and the IgH locus up to several hundred kb," *Hum. Mol. Gen.*, 1992, 1(8):625-632.
Kawasaki et al., "Evolutionary dynamics of the human immunoglobulin κ locus and the germline repertoire of the Vκ genes," *Eur. J. Immunol.*, 2001, 31:1017-1028.

Kawasaki et al., "One-Megabase Sequence Analysis of the Human Immunoglobulin λ Gene Locus," *Genome Res.*, 1997, 7:250-261.

Komatsu et al., "A Variant Chromosome Translocation at 11q13 Identifying *PRAD1*/Cyclin D1 as the *BCL-1* Gene," *Blood*, 1994, 84(4):1226-1231.

Ladanyi et al., "Variant t(8;14) translocations in non-Burkitt's non-Hodgkin's lymphomas," *Blood*, 1992, 79:1377-1379.

Ladanyi et al., "*MYC* Rearrangement and Translocations Involving Band 8q24 in Diffuse Large Cell Lymphomas," *Blood*, 1991, 77(5):1057-1063.

Law et al., "Molecular cytogenetic analysis of chromosomes 1 and 19 in glioma cell lines," *Cancer Genet. Cytogenet.*, 2005, 160:1-14.

Levine et al., "Four New Recurring Translocations in Non-Hodgkin Lymphoma," *Blood*, 1989, 74(5):1796-1800.

Lefranc, "Nomenclature of the Human Immunoglobulin kappa (IGK) Genes," *Exp. Clin. Immunogenet.*, 2001, 18:161-174.

Lenoir et al., "The Use of Lymphomatous and Lymphoblastoid Cell Lines in the Study of Burkitt's Lymphoma," *Burkitt's Lymphoma: A Human Cancer Model*, 1995, pp. 309-318.

Magrath et al., "Burkitt's Lymphoma," *Neoplastic Hematopathology*, 2001, Chapter 27, pp. 953-986.

Manolov et al., "Alternative Involvement of Two Cytogenetically Distinguishable Breakpoints on Chromosome 8 in Burkitt's Lymphoma Associated Translocations," *Cancer Genet. Cytogenet.*, 1986, 20:95-99.

Martín-Subero et al., "Interphase FISH assays for the detection of translocations with breakpoints in immunoglobulin light chain loci," *Int. J. Cancer*, 2002, 98:470-474.

McClure et al., "Adult B-Cell Lymphomas With Burkitt-Like Morphology Are Phenotypically and Genotypically Heterogeneous With Aggressive Clinical Behavior," *Am. J. Surg. Pathol.*, 2005, 26(12):1652-1660.

McKeithan et al., "Molecular cloning of the breakpoint junction of a human chromosomal 8;14 translocation involving the T-cell receptor α-chain gene and sequences on the 3' side of *MYC*," *Proc. Natl. Acad. Sci. USA*, 1986, 83:6636-6640.

O'Connor et al., "Growth factor-dependent differentiation along the myeloid and lymphoid lineages in an immature acute T lymphocytic leukemia," *J. Immunol.*, 1990, 145(11):3779-3787.

Pantou et al., "Cytogenetic Manifestations of Multiple Myeloma Heterogeneity," *Genes, Chromosomes & Cancer*, 2005, 42:44-57.

Park et al., "An (8;14)(q24;q11) Translocation Involving the T-Cell Receptor α-Chain Gene and the *MYC* Oncogene 3' Region in a B-Cell Lymphoma," *Genes, Chromosomes & Cancer*, 1989, 1:15-22.

Poulsen et al., "Detection of illegitimate rearrangements within the immunoglobulin light chain loci in B cell malignancies using end sequenced probes," *Leukemia*, 2002, 16:2148-2155.

Qian et al., "Cyclin D2 promoter disrupted by t(12;22)(p13;q11.2) during transformation of chronic lymphocytic leukaemia to non-Hodgkin's lymphoma," *Br. J. Haematol.*, 1999, 106:477-485.

Rack et al., "Simultaneous Detection of *MYC*, *BVR1*, and *PVT1* Translocations in Lymphoid Malignancies by Fluorescence In Situ Hybridization," *Genes, Chromosomes & Cancer*, 1998, 23:220-226.

Rätsch et al., "Topological Organization of the *MYC/IGK* Locus in Burkitt's Lymphoma Cells Assessed by Nuclear Halo Preparations," *Exp. Cell Res.*, 2002, 273:12-20.

Remstein et al., "Diagnostic utility of fluorescence in situ hybridization in mantle-cell lymphoma," *Br. J. Haematol.*, 2000, 110:856-862.

Rimokh et al., "A Chromosome 12 Coding Region Is Juxtaposed to the *MYC* Protooncogene Locus in a t(8;12)(q24;q22) Translocation in a Case of B-Cell Chronic Lymphocytic Leukemia," *Genes, Chromosomes & Cancer*, 1991, 3:24-36.

Sawyer et al., "Multicolour spectral karyotyping identifies new translocations and a recurring pathway for chromosome loss in multiple myeloma," *Br. J. Haematol.*, 2001, 112:167-174.

Sawyer et al., "Identification of New Nonrandom Translocations in Multiple Myeloma With Multicolor Spectral Karyotyping," *Blood*, 1998, 92(11):4269-4278.

Shaughnessy, Jr. et al., "Cyclin D3 at 6p21 is dysregulated by recurrent chromosomal translocations to immunoglobulin loci in multiple myeloma," *Blood*, 2001, 98:217-223.

Shima et al., "Gene encoding the α chain of the T-cell receptor is moved immediately downstream of *c-myc* in a chromosomal 8;14 translocation in a cell line from a human T-cell leukemia," *Proc. Natl. Acad. Sci. USA*, 1986, 83:3439-3443.

Shou et al., "Diverse karyotypic abnormalities of the *c-myc* locus associated with *c-myc* dysregulation and tumor progression in multiple myeloma," *Proc. Natl. Acad. Sci. USA*, 2000, 97:228-233.

Siebert et al., "Application of Interphase Fluorescence In Situ Hybridization for the Detection of the Burkitt Translocation t(8;14)(q24;q32) in B-Cell Lymphomas," *Blood*, 1998, 91(3):984-990.

Seong et al., "Prognostic value of cytogenetics in multiple myeloma," *Br. J. Haematol.*, 1998, 101:189-194.

Smadja et al., "Chromosomal analysis in multiple myeloma: cytogenetic evidence of two different diseases," *Leukemia*, 1998, 12:960-969.

Weichhold et al., "The Human Immunoglobulin κ Locus Consists of Two Copies That Are Organized in Opposite Polarity," *Genomics*, 1993, 16:503-511.

*WHO Classification of Tumors: Pathology and Genetics of Tumors of Haematopoietic and Lymphoid Tissues*, (Jaffe et al. eds., Lyon: 2001), pp. 31, 110-114, 120-126, 142-156, 164-167, 183, and 260-263.

Willis and Dyer, "The role of immunoglobulin translocations in the pathogenesis of B-cell malignancies," *Blood*, 2000, 96(3):808-822.

Wittekindt et al., "Activation of *c-myc* promoter P1 by immunoglobulin κ gene enhancers in Burkitt lymphoma: functional characterization of the intron enhancer motifs κB, E box 1 and E box 2, and of the 3' enhancer motif PU," *Nucleic Acids Res.*, 2000, 28(3):800-808.

Wlodarska et al., "Philadelphia-Like Translocation t(9;22)(q34;q11) Found in a Follicular Lymphoma Involving not *BCR* and *ABL* but *IGL*-Mediated Rearrangement of an Unknown Gene on 9q34," *Genes, Chromosomes & Cancer*, 1997, 20:113-119.

Wlodarska et al., "Variant t(2;11)(p13;q13) associated with the *IgK-CCND1* rearrangement is a recurrent translocation in leukemic small-cell B-non-Hodgkin lymphoma," *Leukemia*, 2004, 18:1705-1710.

Yabumoto et al., "Rearrangement of the 5' cluster region of the *BCL2* gene in lymphoid neoplasm: a summary of nine cases," *Leukemia*, 1996, 10:970-977.

Yonetani et al., "Heterogeneous Breakpoints on the Immunoglobulin Genes Are Involved in Fusion with the 5' Region of the *BCL2* in B-Cell Tumors," *Jpn. J. Cancer Res.*, 2001, 92:933-940.

Zachau, "The human immunoglobulin κ genes," *Immunoglobulin Genes*, 1995, Chapter 8, pp. 173-191.

Zachau, "The immunoglobulin κ locus—or- what has been learned from looking closely at one-tenth of a percent of the human genome," *Gene*, 1993, 135:167-173.

Zeidler et al., "Breakpoints of Burkitt's Lymphoma t(8;22) Translocations Map Within a Distance of 300 kb Downstrem of *MYC*," *Genes, Chromosomes & Cancer*, 1994, 9:282-287.

Dalla-Favera et al. "Human c-myc onc gene is located on the region of chromosome 8 that is translocated in Burkitt lymphoma cells" *Proc. Natl. Acad. Sci. USA*, vol. 79, 1982; pp. 7824-7827.

* cited by examiner

NUCLEIC ACIDS FOR DETECTING B-CELL MALIGNANCY

CROSS-REFERENCE TO RELATED APPLICATIONS

This application claims the benefit of U.S. Provisional Application Ser. No. 60/799,810, filed May 12, 2006.

BACKGROUND

1. Technical Field

This document relates to methods and materials involved in detecting MYC-immunoglobulin gene rearrangements. For example, this document provides nucleic acids for detecting MYC-immunoglobulin gene rearrangements in mammals.

2. Background Information

MYC-immunoglobulin (IG) gene rearrangements (e.g., translocations) play a major role in the pathogenesis of B-cell lineage malignancy (BCL) by deregulating MYC oncogene expression via juxtaposing a MYC oncogene next to an immunoglobulin regulatory element (e.g., an IG enhancer). The characteristic reciprocal rearrangements in Burkitt lymphoma involve juxtaposing the MYC oncogene next to one of the IG gene loci (e.g., IGH, IGL, or IGK). IG-MYC gene rearrangements have been reported in several other BCL including atypical Burkitt/Burkitt-like lymphoma, diffuse large B-cell lymphoma, follicular lymphoma, mantle cell lymphoma, and multiple myeloma. In non-Hodgkin lymphomas harboring IG-MYC gene rearrangements, the MYC gene rearrangement partner is IGH, IGL, and IGK in approximately 70%, 22%, and 8% of cases, respectively. The location of MYC and IG gene breakpoints vary widely in these rearrangements.

SUMMARY

This document provides methods and materials involved in determining whether or not a sample from a mammal (e.g., a human) contains a MYC-immunoglobulin gene rearrangement. For example, this document provides nucleic acids for detecting MYC-immunoglobulin gene rearrangements. Such nucleic acids can be used to detect a MYC gene rearrangement, an IG gene (e.g., IGH, IGL, or IGK) rearrangement, or both. In some cases, such nucleic acids can be used to identify MYC sequences recombined with immunoglobulin sequences (e.g., IGH, IGK, or IGL). In some cases, such nucleic acids can be used to identify MYC, IGK, or IGL rearrangement junctions. This document also provides methods for determining whether or not a sample from a mammal contains a MYC gene or IG gene rearrangement.

Detecting MYC gene rearrangements can be important for diagnostic and prognostic purposes. Routine detection of MYC gene rearrangements, however, is often hampered by the wide variation in breakpoints in the MYC gene, particularly when a gene other than IGH, such as IGK or IGL, is involved. Identifying MYC gene sequences recombined with immunoglobulin sequences can be used to diagnose B-cell malignancies in mammals. In some cases, identifying MYC gene sequences recombined with immunoglobulin sequences can be used to predict treatment outcome or survival of patients with B-cell malignancies.

In general, one aspect of this document features a probe set comprising, or consisting essentially of, a probe set comprising at least one isolated nucleic acid molecule having the ability to hybridize to a MYC nucleotide sequence and at least one isolated nucleic acid molecule having the ability to hybridize to an IGK nucleotide sequence or an IGL nucleotide sequence. The isolated nucleic acid molecules can comprise a label. The isolated nucleic acid molecule having the ability to hybridize to a MYC nucleotide sequence can comprise a label that is different from the label of the isolated nucleic molecule having the ability to hybridize to an IGK nucleotide sequence or an IGL nucleotide sequence. The labels can be fluorescent. The probe set can comprise at least one isolated nucleic acid molecule having the ability to hybridize to an IGK nucleotide sequence. The probe set can comprise at least one isolated nucleic acid molecule having the ability to hybridize to an IGK nucleotide sequence. The isolated nucleic acid molecules can be greater than 100,000 or 150,000 nucleotides in length.

In a further aspect, this document features a method for detecting the presence or absence of a gene rearrangement, comprising hybridizing to the nucleic acid of a cell a probe set comprising at least one isolated nucleic acid molecule having the ability to hybridize to a MYC nucleotide sequence and at least one isolated nucleic acid molecule having the ability to hybridize to an IGK nucleotide sequence or an IGL nucleotide sequence to form a hybridization pattern; and determining whether or not the hybridization pattern is a pattern of gene rearrangement. The isolated nucleic acid molecules can comprise a label. The isolated nucleic acid molecule having the ability to hybridize to a MYC nucleotide sequence can comprise a label that is different from the label of the isolated nucleic molecule having the ability to hybridize to an IGK nucleotide sequence or an IGL nucleotide sequence. The labels can be fluorescent. The probe set can comprise at least one isolated nucleic acid molecule having the ability to hybridize to an IGK nucleotide sequence. The probe set can comprise at least one isolated nucleic acid molecule having the ability to hybridize to an IGL nucleotide sequence. The isolated nucleic acid molecules can be greater than 100,000 or 150,000 nucleotides in length.

In another aspect, this documents features a method of determining whether or not a mammal has a B-cell lineage malignancy, wherein the method comprises hybridizing a probe set to nucleic acid of a population of cells obtained from a mammal suspected to have said B-cell lineage malignancy to obtain hybridization results, wherein the probe set comprises at least one isolated nucleic acid molecule having the ability to hybridize to a MYC nucleotide sequence and at least one isolated nucleic acid molecule having the ability to hybridize to an IGK nucleotide sequence or an IGL nucleotide sequence; and determining whether or not the hybridization results contain a percentage of cells having a fusion pattern of gene rearrangement that is above a control percentage of cells, where the control percentage is the percentage of cells having the fusion pattern of gene rearrangement for a control mammal not having a B-cell lineage malignancy. The control percentage can be 22% 1R1G1F, 1.5% 2R1G1F, 1.5% 1R2G1F, 1.5% 2R2G1F, or 1.5% 1R1G2F.

In another aspect, this document features an IGL probe set comprising, or consisting essentially of, at least one isolated nucleic acid selected from the group consisting of RP11-47L18, RP11-647D11, and RP11-296H20 and at least one isolated nucleic acid selected from the group consisting of CTD-2503B3, CTD-2306M9, and RP11-947A12.

In another aspect, this document features a probe set comprising, or consisting essentially of, at least one isolated nucleic acid molecule selected from a first group consisting of MYC D-FISH and at least one isolated nucleic acid molecule selected from a second group consisting of IGK D-FISH. The isolated nucleic acid molecules can comprise a label. The isolated nucleic acid molecules selected from the first group can comprise a label that is different from the label of the isolated nucleic molecule selected from the second group. The labels can be fluorescent.

In another aspect, this document features a probe set comprising, or consisting of, at least one isolated nucleic acid molecule selected from a first group consisting of MYC D-FISH and at least one isolated nucleic acid molecule selected from a second group consisting of IGL BAP and IGL D-FISH. The isolated nucleic acid molecules can comprise a label. The isolated nucleic acid molecules selected from the first group can comprise a label that is different from the label of the isolated nucleic molecule selected from the second group. The labels can be fluorescent.

In another aspect, this document features a probe selected from the group consisting of the probes set forth in Table 1.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

This document provides methods and materials involved in assessing gene rearrangements (e.g., translocations). For example, this document provides methods and materials for determining whether or not a sample from a mammal (e.g., a human) contains a MYC gene rearrangement. This document also provides methods and materials for determining whether or not a sample from a mammal (e.g., a human) contains an IG (e.g., an IGH, IGL, or IGK) gene rearrangement. In some cases, the methods and materials provided herein can be used to determine whether or not MYC nucleic acid is recombined with IG nucleic acid. In some cases, the methods and materials provided herein can be used to identify the location of MYC, IGH, IGL, or IGK gene rearrangement breakpoints. Identifying a IG-MYC gene rearrangement can be used to diagnose BCL in a mammal, typically when known clinical symptoms of BCL also are present.

As used herein, the term "BCL" refers to a B-cell lineage malignancy. Examples of BCL include, without limitation, Burkitt lymphoma (BL), multiple myeloma (MM), diffuse large B-cell lymphoma (DLBCL), precursor B-cell acute lymphoblastic leukemia (pre-B ALL), and atypical Burkitt/Burkitt-like lymphoma (BLL).

The term "nucleic acid" as used herein can be RNA or DNA, including cDNA, genomic DNA, and synthetic (e.g. chemically synthesized) DNA. The nucleic acid can be double-stranded or single-stranded. Where single-stranded, the nucleic acid can be the sense strand or the antisense strand. In addition, nucleic acid can be circular or linear.

The term "isolated nucleic acid" as used herein includes any non-naturally-occurring nucleic acid sequence since such non-naturally-occurring sequences are not found in nature and do not have immediately contiguous sequences in a naturally-occurring genome. An isolated nucleic acid can be, for example, a DNA molecule, provided one of the nucleic acid sequences normally found immediately flanking that DNA molecule in a naturally-occurring genome is removed or absent.

In one embodiment, this document provides a collection of nucleic acid molecules (e.g., probes) having the ability to detect a IG-MYC rearrangment. Such collections can contain at least one (e.g., 2, 3, 4, 5, 10, or more) nucleic acid molecule having the ability to hybridize to a MYC nucleotide sequence and at least one (e.g., 2, 3, 4, 5, 10, or more) nucleic acid molecule having the ability to hybridize to an IG nucleotide sequence (e.g., IGH, IGK, or IGL). For example, a collection of isolated nucleic acid molecules provided herein can contain at least one isolated nucleic acid molecule having the ability to hybridize to a MYC nucleotide sequence and at least one isolated nucleic acid molecule having the ability to hybridize to an IGK nucleotide sequence. Examples of isolated nucleic acid molecules having the ability to hybridize to a MYC nucleotide sequence include, without limitation, CTD-2310B16, CTD-2530E12, RP11-367L7, CTD-3056O22, CTD-2267H22, RP11-55J15, RP11-709E21, RP11-654O1, RP11-234A3, RP11-243J12, RP11-460A11, RP11-126N1, CTD-2384G12, RP11-1057N3, RP11-26E5, RP11-259L23, RP11-274M4, and RP11-473O4. Examples of isolated nucleic acid molecules having the ability to hybridize to an IGK nucleotide sequence include, without limitation, RP11-136K15, RP11-316G9, RP11-969D7, RP11-450E9, RP11-525L16, RP11-554H10, RP11-559A1, RP11-50B16, RP11-421K23, RP11-1278P22, RP11-685N3, and RP11-601N4. Collections of isolated nucleic acid molecules having the ability to detect IG-MYC rearrangements can include a vector such as a bacterial artificial chromosome (BAC) or a fosmid. For example, a collection of nucleic acid molecules provided herein can be a collection of BACs containing nucleotide sequences capable of hybridizing to MYC nucleic acid or IG nucleic acid. Isolated nucleic acid molecules having the ability to detect IG-MYC rearrangements can be any length. In some cases, isolated nucleic acid molecules provided herein (e.g., nucleic acid molecules having the ability to detect IG-MYC rearrangements) can be more than 50 bp in length (e.g., more than 100 bp, 250 bp, 500 bp, 1 kb, 2 kb, 5 kb, 7 kb, 10 kb, 20 kb, 50 kb, 100 kb, or 300 kb). Isolated nucleic acid molecules provided herein can have sequences that overlap with another member of the collection. In some cases, each nucleic acid molecule of a collection can have a sequence that is distinct from the sequences of the other members of the collection. The isolated nucleic acid molecules of the collections provided herein can hybridize to MYC or IG nucleotide sequences present in either an intron or an exon. Introns and exons to which isolated nucleic acid molecules having the ability to detect IG-MYC rearrangements can hybridize can be upstream or downstream of the transcription start site or the termination codon of a MYC or IG nucleotide sequence.

One or more of the isolated nucleic acid molecules provided herein can be labeled (e.g., fluorescently, biotin-labeled, antigen-labeled, or radioactively labeled) and used as probes (e.g., fluorescent in situ hybridization (FISH) probes). In some cases, the collections of isolated nucleic acid molecules provided herein can be dual fusion FISH probe sets (e.g., D-FISH probe sets) that can be used to identify gene rearrangement fusion products (e.g., IGL-MYC or IGK-MYC). A D-FISH probe set can have (1) at least one probe that is labeled with a fluorophore (e.g., SpectrumGreen™ or SpectrumOrange™) and that has the ability to hybridize to a nucleotide sequence of one gene (e.g., a MYC gene), and (2) at least another probe that is labeled with a different fluorophore and that has the ability to hybridize to a nucleotide sequence of a second gene (e.g., an IG gene). Such D-FISH probe sets can be used to determine whether 0, 1, or 2 alleles have rearranged. For example, when hybridized in situ to a target gene, a MYC D-FISH probe that is labeled with SpectrumOrange™ and an IGL D-FISH probe that is labeled with SpectrumGreen™ can produce two green foci and two red foci within the nucleus. Such a result can be termed 2R2G and can indicate that neither gene locus is rearranged. In another example, the hybridization described above can produce one green focus, one red focus, and two yellow (e.g., red-green fusion) foci. Such a result can be termed 1R1G2F, or classic D-FISH signal pattern, and can indicate that one allele of each locus is intact and the other MYC allele has recombined with an IGL allele.

In some cases, a collection of isolated nucleic acid molecules provided herein can be a collection of break apart FISH probes (e.g., BAP probes) that can be used to determine the breakpoint in a rearranged gene (e.g., IGL or IGK). In some cases, a BAP probe set can comprise more than one isolated nucleic acid molecule (e.g., more than 2, 3, 4, 5, or more nucleic acid molecules). For example, an IGL BAP probe set can contain one or more RP11-47L18, RP11-647D11, RP11-296H20, CTD-2503B3, CTD-2306M9, or RP11-947A12 nucleic acid molecules. An IGK BAP probe set can contain one or more RP11-136K15, RP11-316G9, RP11-969D7, RP11-450E9, RP11-525L16, RP11-554H10, RP11-559A1, or RP11-50B16 nucleic acid molecules. BAP probe sets can contain at least one isolated nucleic acid molecule that is labeled with a fluorophore and has the ability to hybridize to the centromeric region of a gene and at least one other isolated nucleic acid molecule that is labeled with a different fluorophore and has the ability to hybridize to the telomeric region of the gene. Such BAP probe sets can be hybridized to a target gene locus using in situ hybridization to visualize the breakpoint in a rearranged gene. For example, when hybridized in situ to the target gene, an IGL BAP probe set containing (1) a probe that has the ability to hybridize to the centromeric end of the gene and that is labeled with SpectrumOrange™, and (2) a probe that has the ability to hybridize to the telomeric end of the gene and is labeled with SpectrumGreen™, can produce one red focus, one green focus, and one yellow (e.g., red-green fusion) focus. Such a result can be termed 1R1G1F and can indicate that one IGL allele is intact and the second allele has rearranged at a breakpoint that is between the portion of the probe labeled with SpectrumGreen™ and the portion of the probe labeled with SpectrumOrange™.

SpectrumOrange™-labeled nucleic acid can be used to generate a signal that can be referred to as red ("R"). SpectrumGreen™-labeled nucleic acid can be used to generate a signal that can be referred to as green ("G"). SpectrumAqua™-labeled nucleic acid can be used to generate a signal that can be referred to as aqua ("AQ"). Proximal signals from SpectrumOrange™-labeled nucleic acid and SpectrumGreen™-labeled nucleic acid can combine to form a fusion ("F") signal. Fusion signals can be distinguishable from other signals as adjacent red and green signals or fusion signals can appear as a combined red-green signal (e.g., yellow). It will be understood that the fluorophores used herein can be substituted with alternative sets of distinguishable fluorophores.

In situ hybridization using the nucleic acids provided herein can be performed using any appropriate technique, such as interphase, metaphase, or fiber FISH. Such techniques can be performed on cells of fresh-fixed or paraffin-embedded tissue samples. Cells from any tissue source, such as bone marrow, tonsil, lymph node, or peripheral blood can be used. Microscopy can then be used to detect the presence or absence of a gene rearrangement. In the case of a D-FISH probe set, a gene rearrangement is typically identified by the presence of one or more fusion signals. In the case of a BAP probe set, a gene rearrangement is typically identified by the presence of one or more non-fusion signals (e.g., a red or a green signal). The pattern and size of a signal can be used to estimate the location of a breakpoint. For example, a large non-fusion red signal, a non-fusion green signal and a single fusion signal that are produced when using a BAP probe set containing (1) a probe that has the ability to hybridize to the centromeric end of a gene and that is labeled with SpectrumOrange™, and (2) a probe that has the ability to hybridize to the telomeric end of the gene and is labeled with SpectrumGreen™, can indicate that the break point in that gene is more telomeric than if a small non-fusion red signal, a non-fusion green signal and a single fusion signal were produced.

In some cases, the methods provided herein can be used to determine whether a mammal has BCL. Methods for determining whether a mammal has BCL can include identifying a mammal suspected of having BCL and determining from a tissue sample from that mammal the percentage of cells having a IG-MYC (e.g., IGH-MYC, IGK-MYC, or IGL-MYC) rearrangement. The percentage of cells having a IG-MYC rearrangement can be determined by hybridizing nucleic acid from a tissue sample of the mammal with a BAP probe for MYC, IGH, IGK, or IGL, or a D-FISH probe for IGH-MYC, IGL-MYC, or IGK-MYC, or a combination thereof, and calculating percentage of cells having a IG-MYC rearrangement. In some cases, a mammal suspected of having a BCL can exhibit a known clinical symptom of BCL including, but not limited to, abdominal swelling, enlarged lymph nodes, fatigue, nerve damage, weakness, fever, weight loss, bone pain, anemia, hypercalcemia, abnormal bruising, abnormal bleeding, bone fractures, fever, and frequent infection. A mammal exhibiting a known clinical symptom of BCL and that is found to have a greater percentage of cells having a IG-MYC rearrangement as compared to a mammal that does not have BCL, can be classified as having BCL.

The invention will be further described in the following examples, which do not limit the scope of the invention described in the claims.

EXAMPLES

Example 1

Probe Design

Probes are described with Bacterial Artificial Chromosome (BAC) clone constituents running from the centromere to the telomere ends. Unless specifically mentioned, each clone was determined to be locus-specific by hybridizing a sample of working solution to a normal XY metaphase specimen. Unless specified, IGK and MYC locus-specific clones were selected from the National Center for Biotechnology Information (NCBI) Ensemble map for 2p11.2 and 8q24.1, respectively. IGL locus-specific clones were selected from the University of California Santa Cruz (UCSC) Genome Browser map for 22q11.2. Probes, GenBank accession numbers for probe sequences or sequenced ends, and probe length are set forth below and in Table 1.

TABLE 1

Probes.

| Probe Set | Probe | GenBank accession no. | First nucleotide position | Last nucleotide position | Probe length |
|---|---|---|---|---|---|
| IGK BAP | | | | | |
| Centromeric | RP11-136K15 | AC073416 | 89828899 | 89962428 | 133529 bp |
| | RP11-316G9 | AC009958 | 89619698 | 898308899 | 211201 bp |
| | RP11-969D7 | BH817039 | | | |
| Telomeric | RP11-450E9 | AC062029 | 88736920 | 88866752 | 129832 bp |
| | RP11-525L16 | AC104134 | 88628793 | 88738920 | 110127 bp |
| | RP11-554H10 | AC012671 | 88432099 | 88630793 | 198694 bp |
| | RP11-559A1 | AC104081 | 88369364 | 88511718 | 142118 bp |
| | RP11-50B16 | AC092836 | 88205596 | 88371364 | 165768 bp |
| IGK D-FISH | | | | | |
| | RP11-136K15 | AC073416 | 89828899 | 89962428 | 133529 bp |
| | RP11-316G9 | AC009958 | 89619698 | 898308899 | 211201 bp |
| | RP11-969D7 | BH817039 | | | |
| | RP11-450E9 | AC062029 | 88736920 | 88866752 | 129832 bp |
| | RP11-525L16 | AC104134 | 88628793 | 88738920 | 110127 bp |
| | RP11-554H10 | AC012671 | 88432099 | 88630793 | 198694 bp |
| | RP11-559A1 | AC104081 | 88369364 | 88511718 | 142118 bp |
| | RP11-50B16 | AC092836 | 88205596 | 88371364 | 165768 bp |
| | RP11-421K23 | AC110080 | 89297233 | 89469698 | 172465 bp |
| | RP11-1278P22 | AC116654 | 89180517 | 89299233 | 118716 bp |
| | RP11-685N3 | AC096767 | 89039307 | 89182517 | 143210 bp |
| | RP11-601N4 | AC096579 | 88864752 | 89041307 | 176555 bp |
| IGL BAP | | | | | |
| Centromeric | RP11-47L18 | AQ194866/ AQ194870 | 20256349 | 20442904 | 186555 bp |
| | RP11-647D11 | AQ411280/ AQ404554 | 20357396 | 20545779 | 188383 bp |
| | RP11-296H20 | AZ303172/ AZ303171 | 20521785 | 20694458 | 172673 bp |
| Telomeric | CTD-2503B3 | AQ263966/ AQ263972 | 21649314 | 21837129 | 187815 bp |
| | CTD-2306M9 | AQ015089/ AQ015092 | 21837292 | 21973408 | 136116 bp |
| | RP11-947A12 | AQ564481/ AQ561069 | 21899157 | 22096444 | 197288 bp |
| IGL D-FISH | | | | | |
| prototype | RP11-47L18 | AQ194866/ AQ194870 | 20256349 | 20442904 | 186555 bp |
| | RP11-647D11 | AQ411280/ AQ404554 | 20357396 | 20545779 | 188383 bp |
| | CTD-2503B3 | AQ263966/ AQ263972 | 21649314 | 21837129 | 187815 bp |
| | CTD-2306M9 | AQ015089/ AQ015092 | 21837292 | 21973408 | 136116 bp |
| | RP11-947A12 | AQ564481/ AQ561069 | 21899156 | 22096444 | 197288 bp |
| | RP11-829C4 | AQ800116/ AQ812128 | 20509821 | 20743573 | 233752 bp |
| | RP11-890G10 | AQ813522/ AQ827727 | 20738072 | 20912013 | 173941 bp |
| | WI2-3252A6 | | | | |
| | WI2-3631A14 | | | | |
| | CTD-2036J16 | AQ894131/ AQ894132 | 21019590 | 21165994 | 146404 bp |
| | RP11-114D2 | AQ342516/ AQ342518 | 21101088 | 21266976 | 165888 bp |
| | CTD-3115E23 | AQ152119/ AQ182758 | 21249864 | 21384504 | 134640 bp |
| | RP11-126O14 | AQ347598/ AQ347596 | 21377185 | 21530468 | 153283 bp |
| | CTD-2507C12 | AQ261818/ AQ261819 | 21504619 | 21679711 | 175092 bp |
| | RP11-126O14 | AQ347598/ AQ347596 | 21377185 | 21530468 | 153283 bp |
| | 1000e4 | AC002308 | | | |
| | 142e2 | AC002060 | | | |
| | 865e9 | AC000029 | | | |

TABLE 1-continued

Probes.

| Probe Set | Probe | GenBank accession no. | First nucleotide position | Last nucleotide position | Probe length |
|---|---|---|---|---|---|
| MYC D-FISH | | | | | |
| prototype | CTD-2310B16 | AQ021835/ AQ021832 | 128256001 | 128351766 | 95765 bp |
| | CTD-2530E12 | AQ316551/ AQ353302 | 128346350 | 128551248 | 204898 bp |
| | RP11-367L7 | AQ529915/ AQ529916 | 128528775 | 128696124 | 167349 bp |
| | CTD-3056O22 | AQ100222/ AQ099890 | 128782093 | 128911359 | 129266 bp |
| | CTD-2267H22 | AQ072886/ AQ069562 | 128877510 | 128998081 | 120571 bp |
| | RP11-55J15 | AQ081735/ AQ081737 | 128939466 | 129133580 | 194114 bp |
| | RP11-709E21 | AC007860 | 129133579 | 129319882 | 186203 bp |
| | RP11-654O1 | AC100822 | 129292218 | 129478598 | 186380 bp |
| | RP11-234A3 | AC067844 | 129467587 | 129627690 | 160003 bp |
| | RP11-243J12 | AQ488477/ AQ488474 | 129616022 | 129780642 | 164620 bp |
| | RP11-460A11 | AQ632900/ AQ632870 | 129703153 | 129886892 | 183739 bp |
| | RP11-126N1 | AQ348887/ AQ348888 | 129858417 | 130007078 | 148661 bp |
| | CTD-2384G12 | AQ310297/ AQ310298 | 130049930 | 130185787 | 135857 bp |
| | RP11-1057N3 | AQ673675/ AQ680759 | 130175953 | 130380439 | 204486 bp |
| | RP11-26E5 | AC011257 | 130387747 | 130571979 | 184232 bp |
| | RP11-259L23 | AQ482936/ AQ482939 | 130574587 | 130745615 | 171028 bp |
| | RP11-274M4 | AC022849 | 130745616 | 130900127 | 154511 bp |
| | RP11-473O4 | AC022973 | 130836158 | 131030525 | 194367 bp |
| | RP11-367L7 | AQ529915/ AQ529916 | 128528775 | 128696124 | 167349 bp |
| | CTD-3056O22 | AQ100222/ AQ099890 | 128782093 | 128911359 | 129266 bp |
| | CTD-2267H22 | AQ072886/ AQ069562 | 128877510 | 128998081 | 120571 bp |
| | RP11-55J15 | AQ081735/ AQ081737 | 128939466 | 129133580 | 194114 bp |
| | RP11-709E21 | AC007860 | 129133579 | 129319882 | 186203 bp |
| | RP11-654O1 | AC100822 | 129292218 | 129478598 | 186380 bp |

Example 2

IGK Break Apart Probe (BAP)

A centromeric IGK BAP probe set spanning about 382 kb was labeled with SpectrumOrange™, and an IGK BAP telomeric probe set spanning about 661 kb was labeled with SpectrumGreen™. There was a gap of about 1.4 Mb between the centromeric and telomeric probe sets. The centromeric IGK BAP probe set consisted of three overlapping BAC clones: RP11-136K15, RP11-316G9, and RP11-969D7. The telomeric IGK BAP probe set consisted of five overlapping BAC clones: RP11-450E9, RP11-525L16, RP11-554H10, RP11-559A1, and RP11-50B16.

Example 3

IGK Dual Fusion Probe (D-FISH)

An IGK D-FISH probe set was labeled with SpectrumGreen™. Spanning about 2.6 Mb within the 2p11.2 locus, the IGK D-FISH probe set was composed of 12 pooled BAC clones: RP11-136K15, RP11-316G9, RP11-969D7, separated by about 800 kb and continuing with clones RP11-421K23, RP11-1278P22, RP11-685N3, RP11-601N4, RP11-450E9, RP11-525L16, RP11-554H10, RP11-559A1, and RP11-50B16.

Example 4

IGL BAP

A centromeric IGL BAP probe set spanning about 438 kb was labeled with SpectrumOrange™ and an IGL BAP telomeric probe set spanning about 447 kb was labeled with SpectrumGreen™ with a gap of 955 kb between the centromeric and telomeric probes. The centromeric IGL BAP probe set consisted of end-sequenced BAC clones: RP11-47L18, RP11-647D11, and RP11-296H20. The telomeric IGL BAP probe set consisted of end-sequenced BAC clones: CTD-2503B3, CTD-2306M9, and RP11-947A12.

Example 5

IGL D-FISH

An IGL D-FISH probe set was labeled with SpectrumGreen™. Spanning 1.84 Mb within the 22q11.2 locus, the IGL D-FISH probe set consisted of 14 pooled BAC clones: RP11-47L18, RP11-647D11, RP11-829C4, RP11-890G0, WI2-3252A6, WI2-3631A14, CTD-2036J16, RP11-114D2, CTD-3115E23, RP11-126O14, CTD-2507C12, CTD-2503B3, CTD-2306M9, and RP11-947A12 and two fosmids with locus-specific end sequences: clones WI2-3252A6 (UCSC Genome Browser fosmid end pair No. G248P89282A3) and WI2-3631A14 (UCSC Genome Browser fosmid end pair No. G248P89862A7).

A locus-specific IGL D-FISH probe set prototype used in a pilot study included three fully sequenced BACs from a collection at the University of Oklahoma (BAC clones 1000e4, 142e2, and 865e9), one end-sequenced BAC (RP11-126O14), and a commercial locus-specific BCR gene probe (Vysis, Downers Grove, Ill., Cat. No. 32-192024). The IGL D-FISH probe set prototype was labeled with SpectrumGreen™ and spanned about 743 kb.

Example 6

MYC D-FISH

A MYC D-FISH probe set was labeled with SpectrumOrange™. Spanning 2.774 Mb within the 8q24 locus, the MYC D-FISH probe set contained 18 pooled BAC clones: CTD-2310B16, CTD-2530E12, RP11-367L7, CTD-3056O22, CTD-2267H22, RP11-55J15, RP11-709E21, RP11-654O1, RP11-234A3, RP11-243J12, RP11-460A11, RP11-126N1, CTD-2384G12, RP11-1057N3, RP11-26E5, RP11-259L23, RP11-274M4, and RP11-473O4. With the exception of CTD-2310B16, CTD-2530E12, and RP11-243J12, which are end-sequenced clones selected from the UCSC Genome Browser, all other BAC clones have full sequences registered in GenBank. This BAC D-FISH probe set spans about 562 kb 5' and 2,208 kb 3' from the start and end of the 5,170 base pair MYC oncogene sequence, respectively.

In pilot studies, a MYC D-FISH probe set prototype spanned a total length of about 950 kb, included clones RP11-367L7, CTD-3056O22, CTD-2267H22, RP11-55J15, RP11-709E21, RP11-654O1, and spanned about 656 kb downstream from the 3' end of the MYC gene sequence.

Example 7

MYC BAP and MYC/IGH/CEP8 D-FISH

The Locus Specific Indicator (LSI) MYC Dual Color, Break Apart Rearrangement Probe set (MYC BAP; Vysis Inc., Downers Grove, Ill., catalog no. 32-191096) and the LSI MYC/IGH/CEP8 Tri-color, Dual Fusion Translocation Probe set (Vysis, Inc., catalog no. 32-191020) were used in a probe efficacy study to confirm the presence of a MYC rearrangement (MYC BAP), exclude the presence of an IGH-MYC rearrangement, and assess ploidy as needed (MYC/IGH/CEP8). For the MYC BAP, abnormal signal patterns and cutoffs were as follows: 1R1G1F, 4.5%, 1F, 10%, and 3F, 4.0%. For the LSI MYC/IGH/CEP8 Tri-color, Dual Fusion Translocation Probe set, the cut-offs for classic D-FISH (1R1G2F) is 2.5%, and single-fusion (1R1G1F) was 15.0%.

Example 8

Probe Validation Study

FISH was performed on fresh-fixed and paraffin-embedded tissue samples as described elsewhere (Cataldo, et al., *Am. J. Surg. Pathol.*, 1999; 23(11):1386-92). Analytical sensitivity of each probe set was established by analyzing 20 consecutive metaphases from a normal male (XY) phytohemaglutinin (PHA)-stimulated peripheral blood specimen. To distinguish between normal and abnormal nuclei, strict scoring criteria for each probe set were developed by studying hybridizations on normal and abnormal specimens. Non-overlapping signals were enumerated when the inter-signal distance was greater than three times the estimated signal diameters. In BAP probe sets (RP11-136K15, RP11-316G9, RP11-969D7, RP11-450E9, RP11-525L16, RP11-554H10, RP11-559A1, and RP11-50B16; and RP11-47L18, RP11-647D11, RP11-296H20, CTD-2503B3, CTD-2306M9, and RP11-947A12), these patterns included 1F, 3F, 1R1G1F, 2R2G, 2F1R, and 2F1G. In D-FISH probe sets (RP11-136K15, RP11-316G9, RP11-969D7, RP11-421K23, RP11-1278P22, RP11-685N3, RP11-601N4, RP11-450E9, RP11-525L16, RP11-554H10, RP11-559A1, and RP11-50B16; RP11-136K15, RP11-316G9, RP11-969D7, RP11-421K23, RP11-1278P22, RP11-685N3, RP11-601N4, RP11-450E9, RP11-525L16, RP11-554H10, RP11-559A1, RP11-50B16, 1000e4, 142e2, and 865e9; and CTD-2310B16, CTD-2530E12, RP11-367L7, CTD -3056O22, CTD-2267H22, RP11-55J15, RP11-709E21, RP11-654O1, RP11-234A3, RP11-243J12, RP11-460A11, RP11-126N1, CTD-2384G12, RP11-1057N3, RP11-26E5, RP11-259L23, RP11-274M4, and RP11-473O4), these patterns included 3R2G, 2R3G, 3R3G, 1R1G1F, 2R1G1F, 2R2G1F, and 1R1G2F. A generous inter-signal distance was used to minimize the number of nuclei incorrectly classified as abnormal. In D-FISH probe hybridizations, fusions were enumerated when red and green signals were separated by less than one estimated signal diameter. Using these criteria, normal specimens were hybridized with each FISH probe, blinded, and scored independently by two technologists to establish normal cutoffs. The upper limit of the normal range for each abnormal signal pattern was determined using a one-sided 95% confidence interval for observing the maximum number of nuclei for each false-positive signal pattern seen in 200 scoreable nuclei using binomial distribution (Remstein, et al., *Br. J. Haematol.*, 2000; 110:856-862). Normal cutoffs were calculated using scores from ten normal tonsils (nuclei extracted from paraffin-embedded tissue) and five normal peripheral bloods (fresh-fixed metaphase pellets previously karyotyped as XX or XY). Scores from one additional normal tonsil and one additional normal peripheral blood (XY) were used to verify combined cutoffs for both specimen types. Acceptable cutoffs are summarized in Table 2.

TABLE 2

| STRATEGY/ PROBE Dual Fusion (D-FISH): | Scores UPPER LIMIT OF ABNORMAL % BASED ON A COUNT OF 200 NUCLEI: | | | | | | | |
|---|---|---|---|---|---|---|---|---|
| | 3R2G | 2R3G | 3R3G | 1R1G1F | 2R1G1F | 1R2G1F | 2R2G1F | 1R1G2F |
| MYC(red)/ IGK(green) | 4.5 | 5 | 2.5 | 22 | 1.5 | 1.5 | 1.5 | 1.5 |
| MYC(red)/ IGL(green) | 5 | 6 | 2.5 | 22 | 1.5 | 1.5 | 1.5 | 1.5 |
| Break apart (BAP): | | 1F | 3F | 1R1G1F | 2R2G | 2F1R | 2F1G | |
| IGK 5' (red)/ 3' (green) BAP | | 12.5 | 5 | 6 | 1.5 | 7 | 1.5 | |
| IGL 5' (red)/ 3' (green) BAP | | 13.5 | 4 | 7.5 | 4 | 3 | 2.5 | |

Test specificities were determined for two abnormal positive specimens (nuclei extracted from an IGL-MYC-positive, diffuse large B-cell lymphoma and a fresh-fixed metaphase pellet from a t(2;8)(p11.2;q24.1)-positive multiple myeloma) and three abnormal negative specimens (fresh-fixed metaphase pellets from a t(3;22)(q27;q11.2)-positive B-cell lymphoma, fresh-fixed metaphase pellets from a t(2;7) (p11.2;q22)-positive B-cell lymphoma, and fresh-fixed peripheral blood leukocytes from a BCR-ABL-positive chronic myelogenous leukemia). In all samples, the IGK/ MYC D-FISH probe set (i.e., a combination of IGK D-FISH probes and MYC D-FISH probes), the IGL/MYC D-FISH probe set (i.e., a combination of IGL D-FISH probes and MYC D-FISH probes), the IGK BAP probe set, and IGL BAP probe set produced the expected signal patterns.

Example 9

Probe Efficacy Study

The clinical efficacy of all presently described FISH probes was assessed by testing two t(2;8)(p11.2;q24.1)/IGK-MYC-positive BL cell lines (JI and LY91), two t(8;22)(q24.1; q11.2)/IGL-MYC-positive BL cell lines (BL2 and BL60), and 20 BCL known to have MYC rearrangements not involving IGH for the presence of IGK-MYC or IGL-MYC rearrangements. Cell lines were grown under standard culture conditions. The BCL clinical samples included nine fresh-fixed metaphase pellets with either a t(2;8)(p11.2;q24.1) or t(8;22)(q24.1;q11.2) as determined by previous karyotyping, three paraffin-embedded bone marrow biopsies with contemporaneous t(8;22)(q24.1;q11.2)-positive BM aspirates as determined by prior karyotyping, and eight paraffin-embedded tissues positive by FISH for a MYC rearrangement not involving IGH. Six of the eight paraffin-embedded tissues were previously identified. All BCL met the morphologic and immunophenotypic criteria of the World Health Organization Classification of Tumors of Haematopoietic and Lymphoid Tissues.

Fresh-fixed nuclei were evaluated with MYC BAP and MYC/IGH/CEP8 probe sets as well as either IGK BAP and IGK/MYC probe sets or IGL BAP and IGL/MYC probe sets, depending on karyotype. Isolated nuclei were evaluated using MYC BAP, MYC/IGH/CEP8, IGK BAP, and IGL BAP probe sets since karyotypes had not been performed previously. Following confirmation of MYC and IG gene rearrangements with the BAP probes, each case was hybridized with D-FISH probes for IGK-MYC or IGL-MYC. Specimens were blinded and studied in random order by two microscopists. Using scoring criteria and normal cutoffs established from validation studies, each microscopist scored 100 consecutive qualifying interphase nuclei from different areas of the same slide.

The results of probe this efficacy study are summarized in Table 3. All four BL cell lines were correctly identified as positive for IGK-MYC or IGL-MYC. Of the 20 clinical cases, four were positive for IGK-MYC, twelve were positive for IGL-MYC and four remaining cases had MYC rearrangements involving unknown (non-immunoglobulin) partner genes. Of the twelve cases with a previous karyotype, eight of eight t(8;22)(q24.1;q11.2)-positive specimens had an IGL-MYC rearrangement and three of four t(2;8)(p11.2;q24.1)-positive cases had an IGK-MYC rearrangement. The fourth case, which was positive for the t(2;8) by previous karyotype, was negative for IGK-MYC fusions when assayed using FISH. Metaphase FISH elucidated a MYC rearrangement involving an unknown partner gene on 2p12, which is far telomeric from the IGK locus. Of the eight paraffin-embedded BCL, four were positive for IGL-MYC, one was positive for IGK-MYC, and the three remaining cases had MYC rearrangements involving unknown (non-immunoglobulin) partner genes.

TABLE 3

Probe efficacy.

| Case Type | Case No. | Diagnosis | MYC BAP 5' (red)/ 3' (green) FISH Pattern | MYC(red)/ IGH (green)/ CEP8(aqua) FISH Pattern | IGK BAP 5' (red)/ 3' (green) FISH Pattern | MYC(red)/ IGK(green) FISH Pattern | IGL BAP 5' (red)/ 3' (green) FISH Pattern | MYC(red)/ IGL(green) FISH Pattern | FISH Result |
|---|---|---|---|---|---|---|---|---|---|
| t(2; 8)- Positive Karyotype | 1 | MM | 1R1G1F | 3R2G2AQ | 1R1G1F | 1R1G2F | NA | NA | IGK-MYC |
| | 6 | LY91 Cell Line | 1R1G1F | 3R2G2AQ | 1R1G1F | 1R1G2F | | | IGK-MYC |
| | 7 | JI Cell Line | 1R1G1F | 3R2G2AQ | 1R1G1F | 1R1G2F | | | IGK-MYC |
| | 17 | DLBCL | 2R1G1F | 4R3G3AQ | 2F | 4R2G | | | ? - MYC |
| | 18 | DLBCL | 1R1G1F | 3R2G2AQ | 1R1G1F | 1R1G2F | | | IGK-MYC |
| | 21 | DLBCL | 1R1G1F | 3R2G2AQ | 1R1G1F | 1R1G2F | | | IGK-MYC |
| t(8; 22)- Positive Karyotype | 4 | BL | 1R1G1F | 3R2G2AQ | NA | NA | 1R1G1F | 1R1G2F | IGL-MYC |
| | 8 | BL60 Cell Line | 1R1G1F | 3R2G2AQ | | | 1R1G1F | 1R1G2F | IGL-MYC |
| | 9 | BL2 Cell Line | 1R1G1F | 3R2G2AQ | | | 1R1G1F | 1R1G2F | IGL-MYC |
| | 10 | Pre-BALL | 1R1G1F | 2R3G2AQ | | | 1R1G1F | 1R1G2F | IGL-MYC |
| | 11 | BLL | 1R1G1F | 2R2G2AQ | | | 1R1G1F | 1R1G2F | IGL-MYC |
| | 12 | MM | 1R1G1F | 2R3G2AQ | | | 1R1G1F | 1R1G2F | IGL-MYC |
| | 13 | BL | 1R1G1F | 3R2G2AQ | | | 1R1G1F | 1R1G2F | IGL-MYC |
| | 14 | BL | 2R1G1F | 4R3G3AQ | | | 1R2G1F | 1R1G3F | IGL-MYC |
| | 16 | MM | 1R1G1F | 2R3G2AQ | | | 1R1G1F | 1R1G2F | IGL-MYC |
| | 19 | BLL | 2R1G3-6F | 6-10R6-9G4-7AQ | | | 1R2-3G3F | 5-7R2-3G3-4F | IGL-MYC |
| Paraffin Unknowns | 2 | BLL | 1R1G1F | 3R3G2AQ | 2F | NA | 1R1G1F | 1R1G2F | IGL-MYC |
| | 3 | DLBCL | 2R2G2F | 4R4-6G4AQ | 4F | | 2R2G1F | 2R1G4F | IGL-MYC |
| | 5 | DLBCL | 1R1G1F | 3R2G2AQ | 2F | | 1R1G1F | 1R1G2F | IGL-MYC |
| | 15 | DLBCL | 1R1G1F | 2R2G2AQ | 1R1G1F | 1R1G2F | 2F | NA | IGK-MYC |
| | 20 | BLL | 1R1G1F | 2R3G2AQ | 2F | NA | 1R1G1F | 1R1G2F | IGL-MYC |
| | 22 | BLL | 1R1G2F | 4R4G2AQ | 2F | | 2F | NA | ? - MYC |
| | 23 | BLL | 2R1G1F | 3-4R3G3AQ | 2F | | 2F | | ? - MYC |
| | 24 | DLBCL | 3R1G1F | 5-6R3G4AQ | 2F | | 2F | | ? - MYC |

All four IGK-MYC-positive cases exhibited a classic D-FISH (1R1G2F) signal pattern when assayed using FISH. Of the twelve cases positive for IGL-MYC, nine cases exhibited a classic 1R1G2F D-FISH pattern, two cases exhibited complex D-FISH (i.e., one exhibited a 1R1G3F pattern and one exhibited a 2R1G4F pattern), and one exhibited a very complex polyploid signal pattern with three to four fusions per nucleus.

Example 10

Identification of Breakpoints

A combination of methods, including the direct technique and 48 hour stimulated or unstimulated culture technique, was used to harvest 20 metaphases, whenever possible, in all four cell lines from the probe efficacy study (Example 9) and clinical specimens. All patient karyotypes were characterized according to the Standing Committee on Human Cytogenetic Nomenclature's International System for Human Cytogenetic Nomenclature (ISCN).

Twenty clinical specimens were tested for a MYC rearrangement using two commercially available FISH probe sets: MYC Dual Color, Break Apart Rearrangement Probe set (Vysis) and MYC/IGH/CEP8 probe set (Vysis). Although all 20 clinical cases were positive for a MYC rearrangement using the MYC Dual Color, Break Apart Rearrangement Probe set, a subset of cases (7 of 20) failed to demonstrate a MYC rearrangement using the MYC/IGH/CEP8 probe set. Since IGK-MYC and IGL-MYC rearrangements involve 8q24 breakpoints 3' (downstream) from MYC and the MYC Dual Color, Break Apart Rearrangement Probe set extends 350 kb downstream from MYC, these results indicated that these seven cases (six IGL-MYC-positive and one IGK-MYC-positive) have 8q24 breakpoints greater than 350 kb telomeric (downstream) from MYC.

Initial pilot studies using a prototype IGL/MYC probe set (examples 5 and 6) on one of the seven cases in question (case 10, a t(8;22)(q24.1;q11.2)-positive BCL), demonstrated a classic D-FISH (1R1G2F) signal pattern, but the two fusion signals were very unequal in size. Metaphase FISH localized the small fusion to the der(22)t(8;22)(q24.1;q11.2) chromosome, indicating that the 8q24 breakpoint was likely within the most telomeric BAC (RP11-654O1). Likewise, since the minute truncated green signal associated with the IGL gene locus remained on the der(22)t(8;22)(q24.1;q11.2), the breakpoint on 22q11.2 was likely on the 5' (centromeric) end of the probe sequence. To detect the breakpoints more accurately, the prototype probe sets for MYC and IGL were expanded (2.774 Mb vs. 950 kb, and 1.84 Mb vs. 743 kb, respectively). The BAC clone having the ability to hybridize to the hypothesized breakpoint of each gene was excluded from the respective probe set. Probes were named for the missing BAC clones.

Using the expanded probe sets, breakpoints within the region spanned by the missing clone can yield a 1R1G1F pattern, while breakpoints within the region spanned by the most centromeric (labeled in SpectrumOrange™) or most telomeric (labeled in SpectrumGreen™) probes can yield 2F1R and 2F1G patterns, respectively.

All the MYC breakpoints were localized to a region greater than 350 to 645 kb downstream from the 3' end of MYC (two cases within clone 654O1, 497-645 kb downstream; two cases within clone 709E21, 401-469 kb downstream; and three cases within clone 263C20, greater than 350-469 kb downstream). The IGL breakpoints were localized to variable region gene segments about 97 to 334 kb upstream (5') from the IGL enhancer (two cases within clone RP11-126O14, 97-217 kb upstream; two cases within a region overlapped by clones 126O14 and 3115E23, about 220.5 kb upstream; and two cases within clone 3115E23, 224-334 kb upstream), and the IGK breakpoint was localized to a region less than 50 kb upstream (5') from the intronic and 3' IGK enhancers (within clone 601N4; one case). Table 4 summarizes breakpoint locations for all seven cases.

TABLE 4

MYC, IGL, and IGK breakpoint locations.

| Probe Set | Locus | Centromeric Clones Spectrum-Orange™ | Gap | Telomeric Clones Spectrum-Green™ | Centromeric Probe Size | Telomeric Probe Size |
|---|---|---|---|---|---|---|
| MYC 1 | 8q24.1 | CTD-2310B16<br>CTD-2530E12<br>RP11-367L7<br>CTD-3056O22<br>CTD-2267H22<br>RP11-55J15<br>RP11-263C20 | 68 kb | RP11-654O1<br>RP11-234A3<br>RP11-243J12<br>RP11-460A11<br>RP11-126N1<br>CTD-2384G12<br>RP11-1057N3<br>RP11-26E5 | 968 kb | 1,280 kb |
| MYC 2 | 8q24.1 | CTD-2310B16<br>CTD-2530E12<br>RP11-367L7<br>CTD-3056O22<br>CTD-2267H22<br>RP11-55J15<br>RP11-709E21 | 148 kb | RP11-234A3<br>RP11-243J12<br>RP11-460A11<br>RP11-126N1<br>CTD-2384G12<br>RP11-1057N3<br>RP11-26E5 | 1,064 kb | 1,104 kb |
| IGL 1 | 22q11.2 | RP11-47L18<br>RP11-647D11<br>RP11-829C4<br>RP11-890G10<br>CTD-2036J16<br>RP11-114D2 | 110 kb | RP11-126O14<br>CTD-2507C12<br>CTD-2503B3<br>CTD-2306M9<br>RP11-947A12 | 1,011 kb | 719 kb |
| IGL 2 | 22q11.2 | RP11-47L18<br>RP11-647D11<br>RP11-829C4<br>RP11-890G10<br>CTD-2036J16<br>RP11-114D2<br>CTD-3115E23 | 120 kb | CTD-2507C12<br>CTD-2503B3<br>CTD-2306M9<br>RP11-947A12 | 1,129 kb | 591 kb |
| IGK 1 | 2p11.2 | RP11-421K23<br>RP11-1278P22 | 140 kb | RP11-601N4<br>RP11-450E9<br>RP11-525L16<br>RP11-554H10 | 289 kb | 609 kb |
| IGK 2 | 2p11.2 | RP11-421K23<br>RP11-1278P22<br>RP11-685N3 | 172 kb | RP11-450E9<br>RP11-525L16<br>RP11-554H10<br>RP11-559A1<br>RP11-50B16 | 431 kb | 661 kb |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A probe set for detecting an IG-MYC rearrangement, said set comprising an in situ hybridization probe for a human MYC nucleotide sequence and an in situ hybridization probe for a human IGK nucleotide sequence or a human IGL nucleotide sequence, wherein the nucleotide sequence of said in situ hybridization probe for a human MYC nucleotide sequence is greater than 100,000 nucleotides in length.

2. The probe set of claim 1, wherein said in situ hybridization probe for a human MYC nucleotide sequence comprises a first label and said in situ hybridization probe for a human IGK nucleotide sequence or a human IGL nucleotide sequence comprises a second label, and wherein said first and second labels are different.

3. The probe set of claim 2, wherein said first and second labels are fluorescent.

4. The probe set of claim 1, wherein said probe set comprises said in situ hybridization probe for a human IGK nucleotide sequence.

5. The probe set of claim 1, wherein said probe set comprises said in situ hybridization probe for a human IGL nucleotide sequence.

6. The probe set of claim 1, wherein the nucleotide sequence of said in situ hybridization probe for a human IGK nucleotide sequence is greater than 100,000 nucleotides in length.

7. The probe set of claim 1, wherein the nucleotide sequence of said in situ hybridization probe for a human IGL nucleotide sequence is greater than 100,000 nucleotides in length.

8. The probe set of claim 1, wherein the nucleotide sequence of said in situ hybridization probe for a human MYC nucleotide sequence is greater than 150,000 nucleotides in length.

9. The probe set of claim 1, wherein the nucleotide sequence of said in situ hybridization probe for a human IGK nucleotide sequence is greater than 150,000 nucleotides in length.

10. The probe set of claim 1, wherein the nucleotide sequence of said in situ hybridization probe for a human IGL nucleotide sequence is greater than 150,000 nucleotides in length.

11. A method for detecting the presence or absence of an IG-MYC gene rearrangement, comprising
   (a) performing in situ hybridization using a cell and a probe set to obtain an in situ hybridization pattern, wherein said set comprises an in situ hybridization probe for a human MYC nucleotide sequence comprising a first label and an in situ hybridization probe for a human IGK nucleotide sequence or a human IGL nucleotide sequence comprising a second label, wherein said first label and said second label are different, and
   (b) determining whether or not said in situ hybridization pattern is a pattern of IG-MYC gene rearrangement.

12. The method of claim 11, wherein said labels are fluorescent.

13. The method of claim 11, wherein said method comprises using a probe set comprising said in situ hybridization probe for a human MYC nucleotide sequence and said in situ hybridization probe for a human IGK nucleotide sequence.

14. The method of claim 11, wherein said method comprises using a probe set comprising said in situ hybridization probe for a human MYC nucleotide sequence and said in situ hybridization probe for a human IGL nucleotide sequence.

15. A method of determining whether or not a human has a B-cell lineage malignancy, wherein said method comprises
   (a) performing in situ hybridization using a population of cells obtained from a human suspected to have said B-cell lineage malignancy to obtain in situ hybridization results, wherein said probe set comprises an in situ hybridization probe for a human MYC nucleotide sequence comprising a first label and an in situ hybridization probe for a human IGK nucleotide sequence or a human IGL nucleotide sequence comprising a second label; and
   (b) determining whether or not said in situ hybridization results contain a percentage of cells having a fusion pattern of an IG-MYC gene rearrangement that is above a control percentage of cells, wherein said control percentage is the percentage of cells having said fusion pattern of gene rearrangement for a control human not having said B-cell lineage malignancy.

16. The method of claim 15, wherein said first label comprises a red fluorescent label, and wherein said second label comprises a green fluorescent label.

17. The method of claim 16, wherein said control percentage is 22% 1R1G1F, 1.5% 2R1G1F, 1.5% 1R2G1F, 1.5% 2R2G1F, or 1.5% 1R1G2F.

* * * * *